United States Patent
Kuerner

(10) Patent No.: US 6,794,635 B2
(45) Date of Patent: Sep. 21, 2004

(54) APPARATUS AND METHOD FOR DETECTING AN AMOUNT OF DEPOLARIZATION OF A LINEARLY POLARIZED BEAM

(75) Inventor: Wolfgang Kuerner, Radeburg (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 10/457,706

(22) Filed: Jun. 9, 2003

(65) Prior Publication Data

US 2004/0031909 A1 Feb. 19, 2004

Related U.S. Application Data

(63) Continuation of application No. PCT/EP01/11841, filed on Oct. 12, 2001.

(30) Foreign Application Priority Data

Dec. 7, 2000 (EP) .............................................. 00126888

(51) Int. Cl.[7] .............................. G02F 1/01; G01J 4/00
(52) U.S. Cl. ............. 250/225; 250/559.09; 250/559.46; 356/365
(58) Field of Search ........................... 250/225, 559.01, 250/559.45, 559.46; 348/126; 356/237.2, 237.3, 237.4, 237.5, 364, 365, 366, 367, 368, 369

(56) References Cited

U.S. PATENT DOCUMENTS 5,365,067 A 11/1994 Cole et al.
5,835,220 A 11/1998 Kazama et al.
5,936,726 A 8/1999 Takeda et al.
6,097,488 A * 8/2000 Grek et al. .................. 356/364

FOREIGN PATENT DOCUMENTS

| DE | 24 22 506 A1 | 11/1975 |
| EP | 0 321 836 A2 | 6/1989 |
| EP | 0 838 679 A2 | 4/1998 |
| WO | 98/25131 | 6/1998 |

* cited by examiner

Primary Examiner—Stephone B. Allen
(74) Attorney, Agent, or Firm—Laurence A. Greenberg; Werner H. Stemer; Ralph E. Locher

(57) ABSTRACT

An apparatus and a method for detecting an amount of depolarization of a linearly polarized beam transmitted by a birefringent medium in the direction of the optical axis thereof includes a first beam splitter for separating an on-axis portion of the linearly polarized beam into the orthogonal components, two photodetectors for detecting each component, a second beam splitter for separating an off-axis portion of the linearly polarized beam into the orthogonal components, the second beam splitter being disposed off-axis of the incident linearly polarized beam, a second set of photodetectors for detecting the components separated by the second beam splitter, and a subtracting device for subtracting the signals received by the second set of photodetectors from the respective signals received by the first two photodetectors.

17 Claims, 2 Drawing Sheets

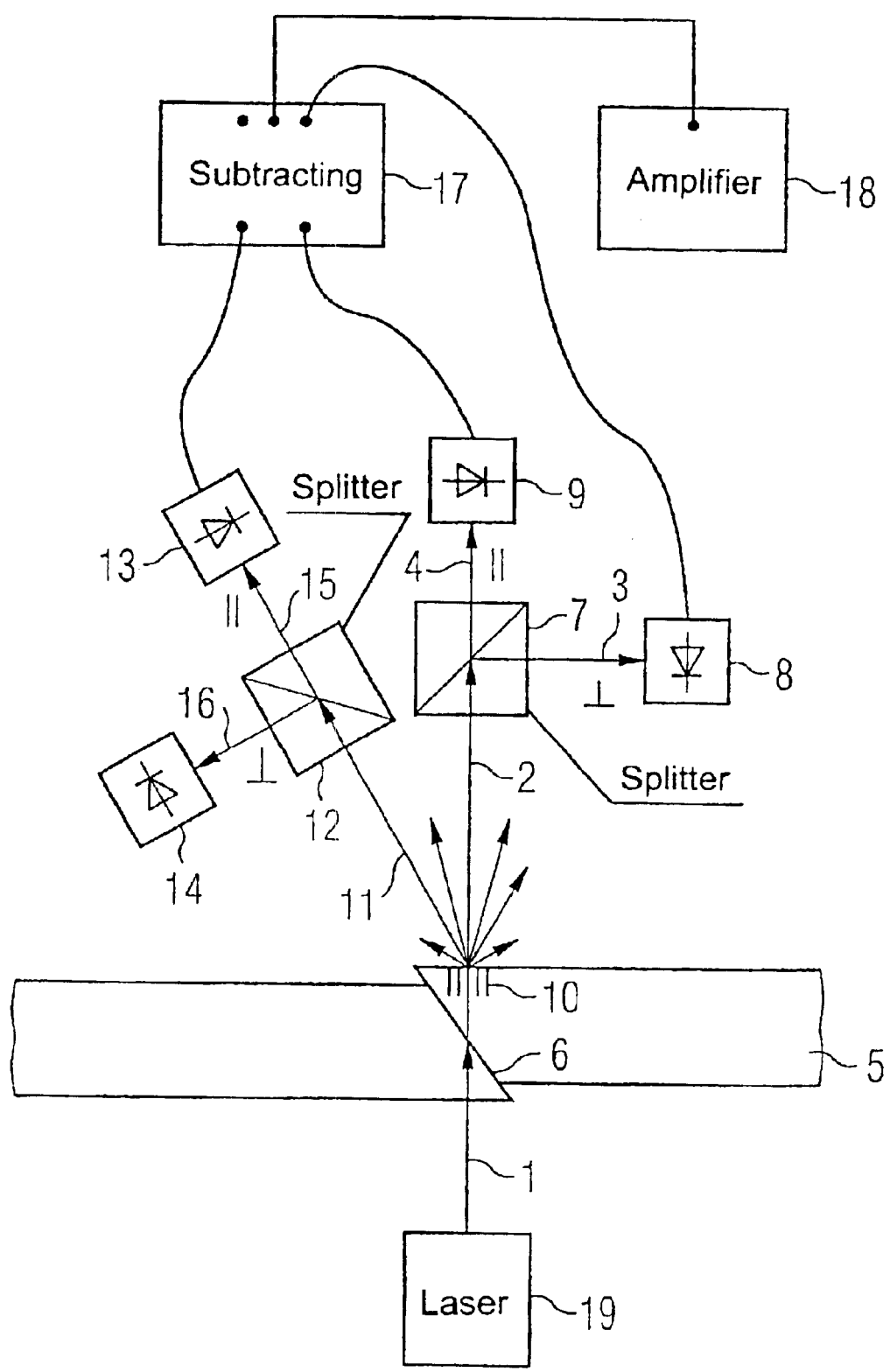

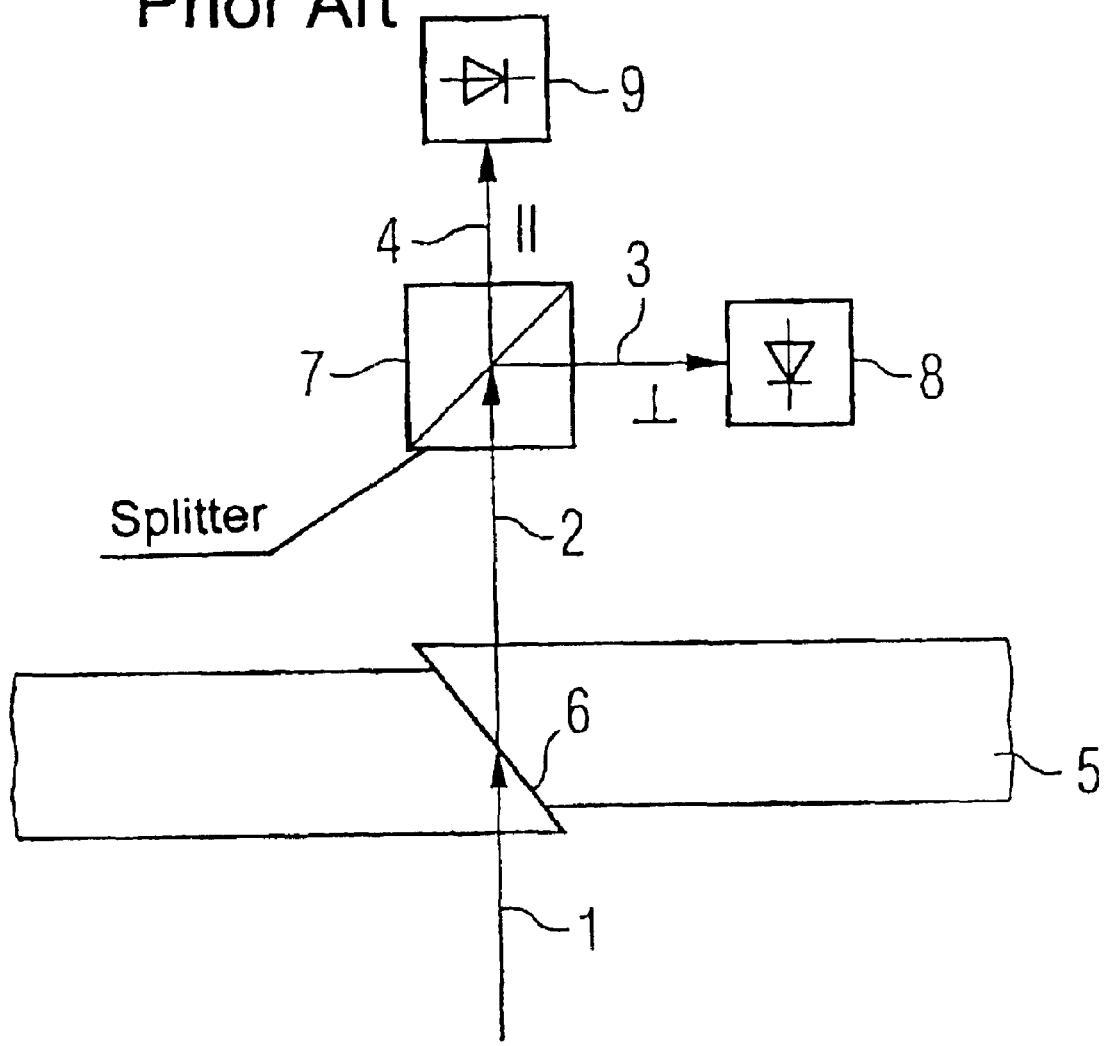

APPARATUS AND METHOD FOR DETECTING AN AMOUNT OF DEPOLARIZATION OF A LINEARLY POLARIZED BEAM

CROSS-REFERENCE TO RELATED APPLICATION

This application is a continuation of copending International Application No. PCT/EP01/11841, filed Oct. 12, 2001, which designated the United States and was published in English.

BACKGROUND OF THE INVENTION

Field of the Invention

The present invention relates to an apparatus and a method for detecting an amount of depolarization of a linearly polarized beam transmitted by a birefringent medium.

This apparatus and method, respectively, can, conveniently, be used for detecting internal stress fields inherent to a semiconductor wafer that normally is isotropic and, thus, does not exhibit any birefringence. As the internal stress fields are induced by dislocations and slip lines, the detection result will be a measure for the amount of dislocations and slip lines and, thus, will be a measure of the quality of the wafer and the resulting semiconductor devices. The linearly polarized beam is, preferably, transmitted by the birefringent medium in a direction perpendicular to the surface of the birefringent medium.

Usually, the manufacture of semiconductor devices involves various steps of wafer processing and, in particular, thermal processing steps during which the wafers are mechanically stressed. As a consequence, dislocations, slides, and slip lines in the crystal are generated that will, for example, cause leakage currents and, thus, tremendously deteriorate the device characteristics. Accordingly, it is necessary to assess the amount of dislocations and slip lines and, based on the result, reject those wafers having an amount of dislocations and slip lines that exceeds a previously determined threshold.

The degree of dislocations and slip lines can be detected by a method called Scanning Infrared Depolarization. The principle of slip line detection by Scanning Infrared Depolarization is based on the fact that linearly polarized light transmitted by a silicon wafer splits up into two orthogonal components, parallel and perpendicular components, with respect to the incident light when internal stress fields lower the symmetry of the crystal from tetrahedral to tetragonal or even lower.

Stated differently, a normally isotropic silicon wafer becomes birefringent when internal stress fields occur. Accordingly, the two orthogonal components form the ordinary and extraordinary beams, respectively, are transmitted with different velocities. As a consequence, the beam emerging from the wafer is elliptically polarized due to the phase difference between the two orthogonal components.

The stress fields occurring in a semiconductor wafer are caused by the distortion of the crystal by dislocations or slip lines. The ratio between the two orthogonal components gives a good measure of the strength of the stress field. An experimental setup for a Scanning Infrared Depolarization measurement is shown in FIG. 2. In FIG. 2, reference numeral 1 denotes a linearly polarized laser beam emitted by a non-illustrated laser device. Reference numeral 2 denotes the laser beam after it has been transmitted by the semiconductor wafer 5. Reference numeral 7 is a polarization beam splitter that splits the incoming beam 2 into the orthogonal components 3 and 4. Component 3 is detected by photodetector 8, and component 4 is detected by photodetector 9. The slip line is represented as a step denoted by reference numeral 6.

The effect described above is very weak. Accordingly, the ratio of the vertical component to the parallel component of the light beam is 1:100 or even less. To detect the weak vertical signal, the amplifier amplifying the photo diode signal has to operate at a very high gain.

However, the perpendicular component detected by the detector is not only caused by the depolarization induced by slip lines but it is also caused by scattering of light. Due to the imperfectness of the wafer surface such as surface roughness or impurities, the polarized light is scattered. In particular, patterns from the semiconductor device, such as trenches and other structures, will cause light scattering. As a consequence, the polarized light will change its polarization direction or will even become unpolarized.

The momentary parallel and perpendicular components of this scattered light will, then, be detected by both detectors. If the amount of scattered light exceeds the true signal by magnitudes, as it is, in particular, the case when the wafers are already patterned, the amplifiers start to work non-linear or are driven into saturation. In both cases, the amplifiers become blind for the weak signal representing the true depolarization effect.

The difficulties arising during a scanning infrared depolarization measurement can partially be avoided when the measurement is performed before structures, such as trenches, that will largely cause light scattering are patterned. However, the amount of dislocations and slip lines will still increase during and after the trench formation because during the trench formation also heat processing steps are performed.

Accordingly, a measurement before the trench formation will cause false measurement results.

Moreover, such a measurement will avoid scattering due to trenches. However, scattering due to impurities or surface roughness cannot be suppressed.

SUMMARY OF THE INVENTION

It is accordingly an object of the invention to provide an apparatus and method for detecting an amount of depolarization of a linearly polarized beam that overcome the hereinafore-mentioned disadvantages of the heretofore-known devices and methods of this general type and that improves the detection of an amount of depolarization of a linearly polarized beam and improves the determination of an internal stress field in a semiconductor wafer.

With the foregoing and other objects in view, there is provided, in accordance with the invention, an apparatus for detecting an amount of depolarization of a linearly polarized beam transmitted by a birefringent medium, including a first beam splitter for separating a first portion of the transmitted beam into orthogonal components, a first set of at least two photodetectors for detecting a respective one of the orthogonal components separated by the first beam splitter, a second beam splitter for separating a second portion of the transmitted beam into orthogonal components, wherein the second beam splitter is disposed off-axis of the incident linearly polarized beam, a second set of at least two photodetectors for detecting a respective one of the orthogonal components separated by the second beam splitter, and a subtracting device for subtracting the signals received by the second set of photodetectors from the respective signals received by the first set of photodetectors.

Preferably, the linearly polarized beam is transmitted in a direction perpendicular to the surface of the birefringent medium and the first portion of the transmitted beam is an on-axis portion and the second portion of the transmitted beam is an off-axis portion.

In accordance with another feature of the invention, the first beam splitter separates an on-axis portion of the transmitted beam into the first orthogonal components and the second beam splitter separates an off-axis portion of the transmitted beam into the second orthogonal components.

In accordance with a further feature of the invention, the linearly polarized beam has an axis and the second beam splitter is disposed at an angle of between approximately 3° and approximately 5° off the axis.

In accordance with an added feature of the invention, there is provided an amplifier connected to the subtracting device, the subtracting device supplying an output signal to the amplifier.

In accordance with an additional feature of the invention, the subtracting device is a lock-in amplifier.

With the objects of the invention in view, there is also provided an apparatus for detecting an amount of depolarization of a linearly polarized beam transmitted by a birefringent medium, including a first beam splitter for separating a first portion of the transmitted beam into first orthogonal components, a first set of at least two photodetectors for detecting a respective one of the first orthogonal components separated by the first beam splitter, the first set of at least two photodetectors producing first output signals, a second beam splitter for separating a second portion of the transmitted beam into second orthogonal components, the second beam splitter being disposed off-axis of the incident linearly polarized beam, a second set of at least two photodetectors for detecting a respective one of the second orthogonal components separated by the second beam splitter, the second set of at least two photodetectors producing second output signals, and a subtracting device connected to the first set of at least two photodetectors and to the second set of at least two photodetectors, the subtracting device subtracting at least one of the second output signals from at least one of the first output signals.

In accordance with yet another feature of the invention, the subtracting device subtracts a respective one of the second output signals from a respective one of the first output signals.

In addition, the present invention provides an apparatus for determining an internal stress field in a semiconductor device including a laser device emitting a linearly polarized infrared laser beam and an apparatus for detecting an amount of depolarization of the linearly polarized infrared laser beam after the laser beam has been transmitted by the semiconductor wafer, the apparatus for detecting an amount of depolarization of the linearly polarized laser beam being as defined above.

With the objects of the invention in view, there is also provided a method for detecting an amount of depolarization of a linearly polarized beam transmitted by a birefringent medium, including the steps of:

separating a first portion of the transmitted beam into orthogonal components by a first beam splitter;
detecting the orthogonal components separated by the first beam splitter by a first set of photodetectors;
separating a second portion of the transmitted beam into orthogonal components by a second beam splitter, wherein the second beam splitter is disposed off-axis of the incident linearly polarized beam;
detecting the orthogonal components separated by the second beam splitter by a second set of photodetectors; and
subtracting the signals received by the second set of photodetectors from the respective signals received by the first set of photodetectors.

In accordance with yet a further mode of the invention, there is provided the step of amplifying a signal resulting from the step of subtracting.

With the objects of the invention in view, there is also provided a method for determining an internal stress field in a semiconductor wafer including the step of irradiating a linearly polarized infrared laser beam into the normally isotropic medium and a method of detecting an amount of depolarization of the linearly polarized laser beam after the infrared laser beam has been transmitted by the semiconductor wafer, wherein the method of detecting an amount of depolarization of the linearly polarized laser beam is as defined above.

The present invention is based upon the understanding that because the effect of light scattering cannot be suppressed and entering of the scattered light into the photo detectors cannot be avoided, this portion of light has to be subtracted from the true signal representing the depolarization due to internal stress before it enters the amplifier.

Other features that are considered as characteristic for the invention are set forth in the appended claims.

Although the invention is illustrated and described herein as embodied in an apparatus and method for detecting an amount of depolarization of a linearly polarized beam, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

FIG. 1 is a block circuit diagram of an experimental setup of the apparatus according to the invention; and FIG. 2 is a block circuit diagram of an experimental setup of a prior art apparatus.

DESCRIPTION OF THE PREFERRED EMBODIMENTS

Referring now to the figures of the drawings in detail and first, particularly to FIG. 1 thereof, there is shown a linearly polarized laser beam having a wavelength of approximately 800 to 900 nm and a beam diameter of 200 nm emitted by a laser device 19, for example, a GaAs laser diode. The laser beam 1 is transmitted by a semiconductor wafer 5. The transmitted laser beam 2 is elliptically polarized and it is split by the beam splitter 7 into two orthogonal components 3 and 4. Component 3 is detected by photodetector 8, and component 4 is detected by photodetector 9. To separate the orthogonal components, the beam splitter 7 is either implemented as a polarization beam splitter or the beam splitter 7 is polarization independent, and the two components 3 and 4 are polarized by a set of orthogonal polarizers, respectively. In the present case, the incidence direction of the laser beam 1 corresponds to the optical axis of the semiconductor wafer 5. The laser beam is directed perpendicular to the surface of the semiconductor wafer.

In addition, a second beam splitter 12 for separating two orthogonal components 15, 16 is positioned a few degrees off-axis so as to separate an off-axis portion 11 of the transmitted laser beam. Moreover, a second set of photodetectors 13, 14 is positioned so that photodetector 13 detects component 15, and photodetector 14 detects component 16.

The off-axis portion 11 of the transmitted laser beam has been scattered by surface roughness, particles or, in particular, device patterns. Because in the off-axis direction only the scattered light will be detected, there is, now, one set of detectors sensitive on both the scattered light as well as the true signal, while one set of detectors is sensitive on the scattered light only. More concretely, the set of detectors 8, 9 detecting the on-axis portion of the transmitted light is sensitive on the scattered light as well as the signal, while the set of detectors 13, 14 detecting the off-axis portion of the transmitted light, is sensitive on the scattered light only.

Reference numeral 17 denotes a subtracting device for subtracting the signals of both sets of detectors resulting in the required true depolarization signal. In particular, the subtracting device subtracts the signal representing the off-axis parallel component from the signal representing the on-axis parallel component. Moreover, the subtracting device subtracts the signal representing the off-axis vertical component from the signal representing the on-axis vertical component. Reference numeral 18 denotes a high gain amplifier that amplifies the resulting difference signals with high gain. The ratio of the vertical component to the parallel component will, then, be a measure for the internal stress in the wafer and, thus, enable a quality evaluation of the wafers.

According to the present invention, by disposing a second beam splitter as well as a second set of photodetectors a few degrees off-axis, the true depolarization signal can be gained and the scattering light effect can be largely suppressed. In particular, scattering items such as impurities, surface roughness, and, especially, device structures such as trenches will no longer impede an exact depolarization measurement. Consequently, it is possible to conduct the Scanning Infrared Depolarization measurement after defining device structures such as trenches. Thus, this measurement will be more exact and substantial than the usually performed measurements before patterning the device structures. Moreover, the effect of impurities and surface roughness can now, advantageously, be suppressed. As a consequence, quality evaluation can be performed at much higher precision.

To ensure that the laser beam is transmitted by the semiconductor wafer, its wavelength has to be appropriately chosen. In particular, an infrared laser beam emitted by a semiconductor laser such as a GaAs laser is, normally, used.

Usually, an experimental setup is chosen in which the laser device is fixed beneath the semiconductor wafer while the detectors as well as the beam splitters are fixed above the semiconductor wafer. The semiconductor wafer is rotated and laterally shifted so that the entire semiconductor wafer is scanned.

When determining the off-axis angle of the second beam splitter, it has to be understood that the scattering angle of light is not isotropic but, rather, lobar. Accordingly, to detect the portion of the scattered light that is also included in the on-axis portion, it is necessary that the displacement angle of the second beam splitter with respect to the optical axis to the semiconductor wafer be very low. However, a minimum angle is determined by the geometric configuration of the apparatus. It was found that an angle of 3° to 5° will provide optimum results.

The accuracy of the measurement as described above can be remarkably improved by using a lock-in amplifier. In such a case, the laser beam irradiated into the semiconductor wafer is chopped with a predetermined frequency. The lock-in amplifier will, then, only select signals from the two sets of detectors which include this predetermined frequency. The lock-in amplifier subtracts the signal supplied by the set of off-axis detectors from the respective signals supplied by the set of on-axis detectors.

The present invention is, in particular, useful when wafers having highly scattering surfaces or various wafer topographies have to be examined.

Although the present invention has been explained with respect to the examination of semiconductor wafers, it is apparent to those skilled in the art that it can be applied to any kind of birefringent materials, in particular, normally isotropic media, having rough and highly scattering surfaces.

I claim:

1. An apparatus for detecting an amount of depolarization of a linearly polarized beam transmitted by a birefringent medium, comprising:
   a first beam splitter for separating a first portion of the transmitted beam into first orthogonal components;
   a first set of at least two photodetectors for detecting a respective one of the first orthogonal components separated by said first beam splitter;
   a second beam splitter for separating a second portion of the transmitted beam into second orthogonal components, said second beam splitter being disposed off-axis of the incident linearly polarized beam;
   a second set of at least two photodetectors for detecting a respective one of the second orthogonal components separated by said second beam splitter; and
   a subtracting device connected to said first set of at least two photodetectors and to said second set of at least two photodetectors, said subtracting device subtracting signals received by said second set of at least two photodetectors from respective signals received by said first set of at least two photodetectors.

2. The apparatus according to claim 1, wherein:
   the birefringent medium has a surface;
   the linearly polarized beam is transmitted in a direction perpendicular to the surface of the birefringent medium; and
   the first portion of the transmitted beam is an on-axis portion and the second portion of the transmitted beam is an off-axis portion.

3. The apparatus according to claim 1, wherein:
   said first beam splitter separates an on-axis portion of the transmitted beam into the first orthogonal components; and
   said second beam splitter separates an off-axis portion of the transmitted beam into the second orthogonal components.

4. The apparatus according to claim 1, wherein:
   the linearly polarized beam has an axis; and
   said second beam splitter is disposed at an angle of between approximately 3° and approximately 5° off the axis.

5. The apparatus according to claim 1, wherein said second beam splitter is disposed at an angle of between approximately 3° and approximately 5° off-axis.

6. The apparatus according to claim 1, further comprising an amplifier connected to said subtracting device, said subtracting device supplying an output signal to said amplifier.

7. The apparatus according to claim 1, wherein said subtracting device is a lock-in amplifier.

8. An apparatus for detecting an amount of depolarization of a linearly polarized beam transmitted by a birefringent medium, comprising:
- a first beam splitter for separating a first portion of the transmitted beam into first orthogonal components;
- a first set of at least two photodetectors for detecting a respective one of the first orthogonal components separated by said first beam splitter, said first set of at least two photodetectors producing first output signals;
- a second beam splitter for separating a second portion of the transmitted beam into second orthogonal components, said second beam splitter being disposed off-axis of the incident linearly polarized beam;
- a second set of at least two photodetectors for detecting a respective one of the second orthogonal components separated by said second beam splitter, said second set of at least two photodetectors producing second output signals; and
- a subtracting device connected to said first set of at least two photodetectors and to said second set of at least two photodetectors, said subtracting device subtracting at least one of said second output signals from at least one of said first output signals.

9. The apparatus according to claim 8, wherein said subtracting device subtracts a respective one of said second output signals from a respective one of said first output signals.

10. An apparatus for determining an internal stress field in a semiconductor wafer, comprising:
- a laser device emitting a linearly polarized infrared laser beam; and
- an apparatus for detecting an amount of depolarization of the linearly polarized infrared laser beam after the laser beam has been transmitted by the semiconductor wafer, said apparatus having:
  - a first beam splitter for separating a first portion of the transmitted beam into first orthogonal components;
  - a first set of at least two photodetectors for detecting a respective one of the first orthogonal components separated by said first beam splitter;
  - a second beam splitter for separating a second portion of the transmitted beam into second orthogonal components, said second beam splitter being disposed off-axis of the incident linearly polarized beam;
  - a second set of at least two photodetectors for detecting a respective one of the second orthogonal components separated by said second beam splitter; and
  - a subtracting device connected to said first set of at least two photodetectors and to said second set of at least two photodetectors, said subtracting device subtracting signals received by said second set of at least two photodetectors from respective signals received by said first set of at least two photodetectors.

11. A method for detecting an amount of depolarization of a linearly polarized beam transmitted by a birefringent medium, which comprises:
- separating a first portion of the transmitted beam into first orthogonal components with a first beam splitter;
- detecting the first orthogonal components separated by the first beam splitter with a first set of photodetectors;
- separating a second portion of the transmitted beam into second orthogonal components with a second beam splitter, the second beam splitter being disposed off-axis of the incident linearly polarized beam;
- detecting the second orthogonal components separated by said second beam splitter with a second set of photodetectors; and
- subtracting the signals received by the second set of photodetectors from the respective signals received by the first set of photodetectors.

12. The method according to claim 11, which further comprises transmitting the linearly polarized beam in a direction perpendicular to a surface of the birefringent medium, the first portion of the transmitted beam being an on-axis portion and the second portion of the transmitted beam being an off-axis portion.

13. The method according to claim 11, which further comprises amplifying a signal resulting from the step of subtracting.

14. The method according to claim 12, which further comprises amplifying a signal resulting from the step of subtracting.

15. A method for determining an internal stress field in a semiconductor wafer, which comprises:
- irradiating a linearly polarized infrared laser beam into the semiconductor wafer; and
- detecting an amount of depolarization of the laser beam after the laser beam has been transmitted by the semiconductor wafer by:
  - separating a first portion of the transmitted beam into first orthogonal components with a first beam splitter;
  - detecting the first orthogonal components separated by the first beam splitter with a first set of photodetectors;
  - separating a second portion of the transmitted beam into second orthogonal components with a second beam splitter, the second beam splitter being disposed off-axis of the incident linearly polarized beam;
  - detecting the second orthogonal components separated by said second beam splitter with a second set of photodetectors; and
  - subtracting the signals received by the second set of photodetectors from the respective signals received by the first set of photodetectors.

16. The method according to claim 15, which further comprises transmitting the linearly polarized beam in a direction perpendicular to a surface of the birefringent medium, the first portion of the transmitted beam being an on-axis portion and the second portion of the transmitted beam being an off-axis portion.

17. The method according to claim 15, which further comprises amplifying a signal resulting from the step of subtracting.

* * * * *

UNITED STATES PATENT AND TRADEMARK OFFICE
CERTIFICATE OF CORRECTION

PATENT NO. : 6,794,635 B2
DATED : September 21, 2004
INVENTOR(S) : Wolfgang Kuerner It is certified that error appears in the above-identified patent and that said Letters Patent is hereby corrected as shown below:

<u>Title page,</u>
Item [73], Assignee, should read as follows:
-- Infineon Technologies SC300 GmbH & Co. KG --

Signed and Sealed this

Twenty-first day of December, 2004

JON W. DUDAS
*Director of the United States Patent and Trademark Office*